United States Patent
Mikami et al.

[11] Patent Number: 5,811,565
[45] Date of Patent: Sep. 22, 1998

[54] METHOD FOR PURIFYING 3-METHACRYLOXYPROPYLDIMETHYL-HALOSILANES AND 3-METHACRYLOXY-PROPYLMETHYLDIHALOSILANES

[75] Inventors: Ryuzo Mikami; Tadashi Okawa, both of Chiba Prefecture, Japan

[73] Assignee: Dow Corning Toray Silicone Co., Ltd., Tokyo, Japan

[21] Appl. No.: 837,694

[22] Filed: Apr. 22, 1997

[30] Foreign Application Priority Data

Apr. 26, 1996 [JP] Japan .................................. 8-131433

[51] Int. Cl.$^6$ ........................................................ C07F 7/08
[52] U.S. Cl. ............................................................. 556/440
[58] Field of Search ............................................... 556/440

[56] References Cited

U.S. PATENT DOCUMENTS 5,262,555  11/1993  Okawa et al. ............................ 556/440

FOREIGN PATENT DOCUMENTS 01-098631   4/1989   Japan .
06-184309   7/1994   Japan .

*Primary Examiner*—Paul F. Shaver
*Attorney, Agent, or Firm*—William F. Boley

[57] ABSTRACT

A method for purifying 3-methacryloxypropyl-dimethylhalosilane or 3-methacryloxypropylmethyldihalosilane comprising adding (A) a Lewis acid halide to (B) 3-methacryloxypropyldimethylhalosilane or 3-methacryloxypropyl-methyldihalosilane obtained from an addition reaction of (a) allyl methacrylate and (b) dimethylhalosilane or methyldihalosilane, where the addition reaction by-products contained in aforementioned component (B), 1-methyl-2-methacryloxyethyldimethylhalosilane or 1-methyl-2-methacryloxyethylmethyldihalosilane, are decomposed and the decomposition products produced are then separated by distillation.

14 Claims, No Drawings

METHOD FOR PURIFYING 3-METHACRYLOXYPROPYLDIMETHYL-HALOSILANES AND 3-METHACRYLOXY-PROPYLMETHYLDIHALOSILANES

BACKGROUND OF INVENTION

The present invention relates to a method for purifying 3-methacryloxypropyldimethylhalosilanes and 3-methacryloxypropyl-methyldihalosilanes obtained by an addition reaction of allyl methacrylate and dimethylhalosilane or methyldihalosilane. 3-Methacryloxypropyldimethylhalosilanes and 3-methacryloxypropyl-methyldihalosilanes are used as raw materials for radical-copolymerizable silicone macromonomers. This type of methacryloxypropyl functional halosilane is synthesized by means of an addition reaction of allyl-methacrylate and dimethylhalosilane or methyldihalosilane. For example, Polymer, 26, 437 (1985), describes a method where after an addition reaction of allylmethacrylate and dimethylchlorosilane, 3-methacryloxypropyldimethylchlorosilane is recovered by distillation. However, a problem with this addition reaction is the formation of the β-addition compound 1-methyl-2-methacryloxyethyldimethylchlorosilane as a by-product. Moreover, as the boiling points of 3-methacryloxypropyldimethylchlorosilane and 1-methyl-2-methacryloxyethyldimethylchlorosilane are close, it was difficult to remove the by-product 1-methyl-2-methacryloxyethyl- dimethylchlorosilane by means of distillation.

While conducting research on a method for removing the aforementioned by-product to obtain high-purity 3-methacryloxypropyldimethylhalosilane or 3-methacryloxypropyl-methyldihalosilane, the inventors of the present invention discovered that, as shown in the following chemical reaction formulas, methacryloxydimethylchlorosilane (2) and dimethyldichlorosilane (4) were contained as bifunctional impurities in 3-methacryloxypropyl dimethylchlorosilane containing as a by-product the β-addition compound 1-methyl-2-methacryloxyethyldimethylchlorosilane. It is thought that this β-addition compound can impart bifunctional impurities by means of the following decomposition reaction and exchange reaction.

Chemical reaction 1

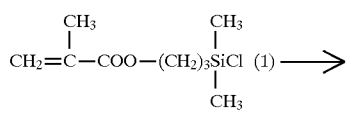

Chemical reaction 2

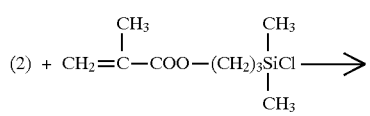

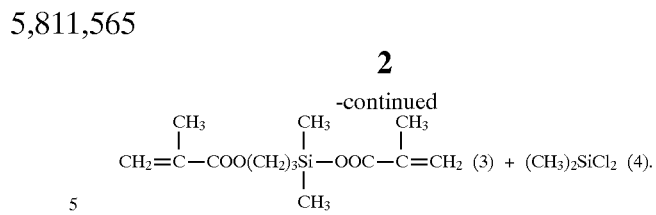

However, the factor triggering this decomposition reaction was unknown. For example, even when 3-methacryloxypropyl-dimethylchlorosilane containing an addition reaction by-product was aged for long periods at high temperatures, it was virtually impossible to decompose the β-addition compound 1-methyl-2-methacryloxyethyldimethylchlorosilane. When 3-methacryloxypropyldimethylchlorosilane containing this β-addition product and bifunctional impurities is subjected to a condensation reaction together with, for example, polydimethylsiloxane having one terminal of the molecule terminated with a silanol group, such as described in Japanese Unexamined Patent Application No. H1-98631, a radical-copolymerizable silicone macromonomer containing non-radical-polymerizable polydimethylsiloxane as an impurity was obtained by the following reactions.

Chemical reaction 3

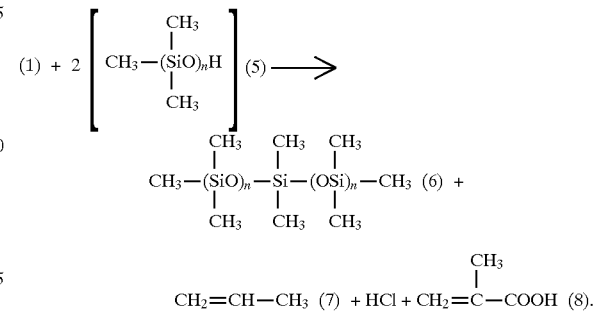

Chemical reaction 4

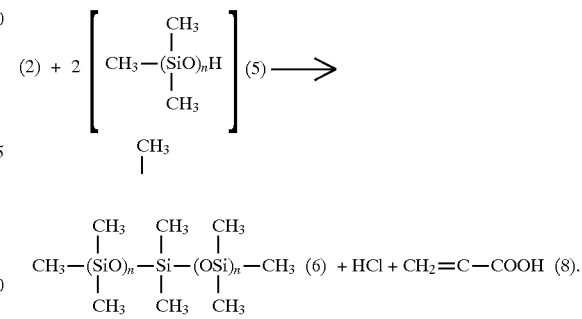

Chemical reaction 5

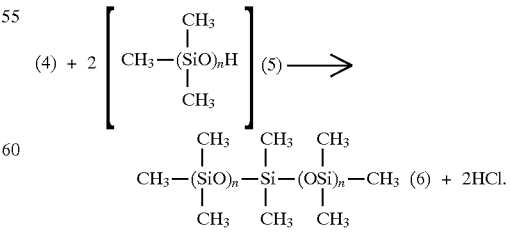

As presented in Japanese Unexamined Patent Application No. H6-184309, graft copolymers produced in this manner derived from radical-copolymerizable silicone macromonomer containing as an impurity non-radical-polymerizable polydimethylsiloxane had the problems of a decrease in the silicone macromonomer copolymerization ratio and the occurrence of bleeding of the film due to free polydimethylsiloxane. For this reason, there was a demand for high-purity radical polymerizable silicone macromonomer and there was a demand for a method for manufacturing its raw materials 3-methacryloxypropyl-dimethylhalosilane or 3-methacryloxypropylmethyldihalosilane.

The purpose of the present invention is to provide a method for purifying 3-methacryloxypropyldimethylhalosilane or 3-methacryloxypropylmethyldihalosilane in which 1-methyl-2-methacryloxyethyldimethylhalosilane or 1-methyl-2-methacryloxyethylmethyldihalosilane, which are addition reaction by-products contained in 3-methacryloxypropyldimethylhalosilane or 3-methacryloxypropylmethyldihalosilane obtained by an addition reaction, can be selectively and completely removed.

SUMMARY OF INVENTION

The present invention is a purification method comprising adding (A) a Lewis acid halide to (B) 3-methacryloxypropyl-dimethylhalosilane or 3-methacryloxypropylmethyldihalosilane obtained from an addition reaction of (a) allyl methacrylate and (b) dimethylhalosilane or methyldihalosilane, where the addition reaction by-products contained in aforementioned component (B), comprising 1-methyl-2-methacryloxyethyldimethylhalosilane or 1-methyl-2-methacryloxyethylmethyldihalosilane are decomposed, and the decomposition products are then separated by distillation. The present method allows high-purity 3-methacryloxypropyldimethylhalosilane or 3-methacryloxypropyl methyldihalosilane to be manufactured with good yield.

DESCRIPTION OF INVENTION

The present invention relates to a method for purifying 3-methacryloxypropyldimethylhalosilanes and 3-methacryloxypropyl-methyldihalosilanes. The method comprises adding (A) a Lewis acid halide to (B) 3-methacryloxypropyldimethylhalosilane or 3-methacryloxypropylmethyldihalosilane obtained from an addition reaction of (a) allylmethacrylate and (b) dimethylhalosilane or methyldihalosilane, where the addition reaction by-products contained in aforementioned component (B) comprising 1-methyl-2- methacryloxyethyl dimethylhalosilane or 1-methyl-2-methacryloxyethylmethyl dihalosilane are decomposed, and the decomposition products are then separated by distillation. The 3-methacryloxypropyldimethylhalosilane or 3-methacryloxypropylmethyldihalosilane comprising component (B) used in the present method is obtained by means of an addition reaction of (a) allylmethacrylate and (b) dimethylhalosilane or methyldihalosilane, that is a silane having the formula $H(CH_3)_nSiX_{3-n}$, where in the formula X denotes a halogen atom and n is the integer 1 or 2. The compounds shown below are examples of this type of halosilane, but among these compounds, the use of chlorosilane, which is easy to obtain, is preferred.

$H(CH_3)_2SiF$ (9)
$H(CH_3)_2SiCl$ (10)
$H(CH_3)_2SiBr$ (11)
$H(CH_3)_2SiI$ (12)
$H(CH_3)SiF_2$ (13)
$H(CH_3)SiCl_2$ (14)
$H(CH_3)SiBr_2$ (15)
$H(CH_3)SiI_2$ (16)

Complexes and compounds of transition metals such as platinum, palladium, rhodium, ruthenium, cobalt, and nickel can be used, for example, as addition reaction catalysts for causing component (a) and component (b) to undergo an addition reaction. Preferred examples of such addition reaction catalysts are platinum-type catalysts such as chloroplatinic acid, chloroplatinic acid dissolved in alcohol, ketone, or ether; complexes of chloroplatinic acid and olefins; complexes of chloroplatinic acid and alkenylsiloxanes; and supported platinum black and platinum. Moreover, this addition reaction may be carried out in the presence of an organic solvent or a conventionally-known polymerization inhibitor. Examples of such polymerization inhibitors include those presented in Japanese Unexamined Patent Applications S63-188689, H4-103588, H4-117389, H4-117390, H4-124192, H4-128292, H4-128293, and H4-128294. Reaction products obtained in such a reaction necessarily contain the reaction by-products 1-methyl-2-methacryloxyethyl-dimethylhalosilane or 1-methyl-2-methacryloxyethylmethyl-dihalosilane.

Specific examples of the Lewis acid halide comprising component (A) used in the present method include halides of elements such as beryllium, boron, aluminum, phosphorus, calcium, titanium, vanadium, chromium, iron, cobalt, copper, zinc, gallium, zirconium, molybdenum, cadmium, indium, tin, antimony, tellurium, tantalum, tungsten, mercury, and bismuth. These Lewis acid halides should preferably be composed of halogen atoms which are the same as the halogen atoms of the 3-methacryloxypropyldimethylhalosilane or 3-methacryloxypropyl-methyldihalosilane.

There are cases in which halides having strong Lewis acidity such as aluminum (III) chloride, iron (II) chloride, and zinc (II) chloride break bonds between silicon atoms and methyl groups under harsh conditions and can even effect decomposition of 3-methacryloxypropyldimethylhalosilane or 3-methacryloxypropylmethyldihalosilane. Therefore, when using such strong Lewis acid halides attention must be paid to the reaction conditions. Preferred examples of the Lewis acid halides of component (A) include comparatively weak-Lewis-acidity tin (IV) chloride, titanium (IV) chloride, beryllium (II) chloride, antimony (V) chloride, mercury (II) chloride, copper (II) chloride, bismuth (II) chloride, cobalt (II) chloride, calcium (II) chloride, and cadmium (II) chloride. Among these substances, the inventors of the present invention feel that the use of copper (II) chloride, a polymerization inhibitor of 3-methacryloxypropyl functional halosilanes first presented in Japanese Unexamined Patent Application No. H5-271248, is particularly desirable. The reason is that ordinarily, heat treatment is necessary for breaking down the aforementioned β-addition compound, and copper (II) chloride is also effective in polymerization inhibition during such heat treatment. Even when heat treatment was carried out in the presence of copper (II) chloride, a period of over 10 hours was required to completely decompose the β-addition compounds 1-methyl-2-methacryloxyethyl-dimethylhalosilane or 1-methyl-2-methacryloxyethylmethyl-dihalosilane. Specifically, even when copper (II) chloride, a polymerization inhibitor in distillation purification of 3-methacryloxypropyldimethylhalosilane or 3-methacryloxypropyl-methyldihalosilane presented in Japanese Unexamined Patent Application No. H5-271248 by the authors of the present invention, was used, distillation of the target silane required only 1 to 2 hours, and it was not possible during this period to completely decompose the aforementioned β-addition product. It could not be predicted that a halide such as copper chloride would be effective both in its action of inhibition of polymerization and its action of decomposing β-addition products.

The amount of the Lewis acid halide comprising component (A) used is thought to depend on the conditions of the aforementioned β-addition product decomposition reaction, but it should be 0.01 to 20 parts by weight per 100 parts by weight of the 3-methacryloxypropyl- dimethylhalosilane or 3-methacryloxypropylmethyldihalosilane obtained in the addition reaction. A range of 0.1 to 10 parts by weight is preferred. This β-addition product decomposition reaction should preferably be carried out without a solvent, but it may also be carried out in the presence of an organic solvent. The decomposition reaction may be carried out at room temperature or under conditions of heating at a temperature within a range of 50° to 2000° C.

In the present method, after the 1-methyl-2-methacryloxyethyldimethylsilane or 1-methyl-2-methacryloxyethylmethyldihalosilane which is an addition reaction by-product contained in the aforementioned component (B) has been treated and broken down by the Lewis acid halide comprising component (A), the decomposition product formed is distilled and separated. But, since the methacryloxydimethylhalosilane or methacryloxymethyldihalosilane, propene, dimethyl dihalosilane, methyltrihalosilane decomposition products produced in this decomposition reaction are compounds having a lower boiling point than the aforementioned 3-methacryloxypropyldimethylhalosilane or 3-methacryloxypropyl-methyldihalosilane, they can be removed by distillation. Specifically, after the β-addition product which is a by-product of the addition reaction is selectively and completely decomposed and this low-boiling-point decomposition product is removed by distillation, high-purity 3-methacryloxypropyldimethylhalosilane or 3-methacryloxypropylmethyldihalosilane can then be obtained by distillation and separation. Here, a conventionally-known polymerization inhibitor may be used in order to inhibit a polymerization reaction of 3-methacryloxypropyl-dimethylhalosilane or 3-methacryloxypropylmethyldihalosilane during distillation purification. Examples of useful polymerization inhibitors include phenothiazine, hindered phenol compounds, amine compounds, quinone compounds, and oxygen.

The following is an explanation of the present invention by means of practical examples. In the practical examples, Me is a methyl group.

PRACTICAL EXAMPLE 1

100 g (794 millimoles) Of allyl methacrylate and 0.1 g of 3,5-di-t-butyl-4-hydroxyphenylmethyl dimethyl ammonium chloride were added to a 4-necked flask equipped with an agitator and a complex of platinum and 1,2-divinyltetramethyldisiloxane in an amount of 20 ppm of the platinum metal with respect to the weight of the allyl methacrylate was mixed in. This mixture was heated to 90° C. in a nitrogen atmosphere and a small amount of dimethylchlorosilane was added dropwise. After it was confirmed that the reaction had begun, while maintaining the reaction temperature at 85° to 950C. by cooling, 68.2 g (722 millimoles) of dimethylchlorosilane was added dropwise. After this dropwise addition was completed, stirring was carried out for 30 minutes at 80° C. Next, 0.1 g of 2,6-di-t-butyl-4-methylphenol was added, distillation was carried out under a reduced pressure of 5 mmHg, and fractions were taken at 92° to 105° C. 126.1 g Of the product was obtained (yield: 79%). The results of carbon ($^{13}$C NMR) and silicon nuclear magnetic resonance analysis ($^{29}$Si NMR) showed that this fraction had the composition shown in Table 1.

1 g of copper (II) chloride was added to 66.6 g of this fraction, and heating and stirring were carried out in a nitrogen atmosphere at 100° C. Samples were taken at specified intervals and the content of 1-methyl-2-methacryloxyethyldimethylchlorosilane was monitored by 13C NMR analysis. The content of 1-methyl-2-methacryloxyethyldimethylchlorosilane was 0.37% after 8 hours and 0.2% after 10 hours, with complete disappearance after 12 hours. The composition after 12 hours is shown in Table 1.

0.01 g Of 2,6-di-t-butyl-4-methylphenol was added to this chlorosilane mixture, distillation was carried out at a reduced pressure of 5 mmHg, and 61 g of a fraction distilling at 97 ° to 105° C. was obtained. The results of $^{13}$C NMR and $^{29}$Si NMR analysis showed that this fraction had the composition shown in Table 1.

COMPARISON EXAMPLE

With the exception that the copper (II) chloride of Practical Example 1 was not added and heating and stirring were carried out in dry air, heating and stirring were carried out in the same manner as in Practical Example 1. When the reaction product was sampled and analyzed by means of $^{13}$C NMR and $^{29}$Si NMR, the results shown in Table 2 were obtained.

PRACTICAL EXAMPLE 2

Before the treatment with copper (II) chloride carried out in Practical Example 1, 0.15 g of iron (II) chloride was added to 10 g of 3-methacryloxypropyl-dimethylchlorosilane, and heating and stirring were carried out in dry air at 100° C. for 8 hours. When the reaction product was sampled and analyzed by means of $^{13}$C NMR, no 1-methyl-2-methacryloxyethyldimethylchlorosilane was detected. Moreover, when the fraction obtained by heating and reduced-pressure distillation was analyzed, it was shown that the main component of this fraction was methacryloxypropyl- dimethylchlorosilane and that it did not contain 1-methyl-2-methacryloxyethyldimethylchlorosilane.

PRACTICAL EXAMPLE 3

Before the treatment with copper (II) chloride carried out in Practical Example 1, 0.15 g of zinc chloride was added to 10 g of 3-methacryloxypropyl-dimethylchlorosilane, and heating and stirring were carried out in dry air at 100° C for 8 hours. When the reaction product was sampled and analyzed by means of $^{13}$C NMR, no 1-methyl-2-methacryloxyethyldimethylchlorosilane was detected. Moreover, when the fraction obtained by heating and reduced-pressure distillation was analyzed, it was shown that the main component of this fraction was methacryloxypropyldimethylchlorosilane and that it did not contain 1-methyl-2-methacryloxyethyl-dimethylchlorosilane.

PRACTICAL EXAMPLE 4

Before the treatment with copper (II) chloride carried out in Practical Example 1, 0.15 g of cobalt chloride was added to 10 g of 3-methacryloxypropyl-dimethylchlorosilane, and heating and stirring were carried out in a nitrogen atmosphere at 100° C for 8 hours. When the reaction product was sampled and analyzed by $^{13}C$ NMR, no 1-methyl-2-methacryloxyethyldimethylchlorosilane was detected. Moreover, when the fraction obtained by heating and reduced-pressure distillation was analyzed, it was shown that the main component of this fraction was methacryloxypropyldimethylchlorosilane and that it did not contain 1-methyl-2-methacryloxyethyl-dimethylchlorosilane.

TABLE 1

|  | Before treatment | After 12 hours | After distillation |
|---|---|---|---|
| $CH_2=CCOO(CH_2)_3SiCl$ with Me, Me, Me substituents | 93.1% | 93.1% | 98.5 |
| $CH_2=CCOOCH_2CH-SiCl$ with Me, Me, Me, Me substituents | 2.4 | 0 | 0 |
| $Me_2SiCl_2$ | 0.8 | 1.1 | 0 |
| $CH_2=CCOO-SiCl$ with Me, Me, Me substituents | 0.6 | 0.7 | 0 |
| $CH_2=CCOO(CH_2)_3SiOOCC=CH_2$ with Me, Me, Me substituents | 1.3 | 2.0 | 0.4 |
| Other components | 1.8 | 3.1 | 1.1 |

TABLE 2

|  | Before treatment | After 12 hours |
|---|---|---|
| $CH_2=CCOO(CH_2)_3SiCl$ with Me, Me, Me substituents | 93.1% | 93.1% |
| $CH_2=CCOOCH_2CH-SiCl$ with Me, Me, Me, Me substituents | 2.4 | 2.2 |
| $Me_2SiCl_2$ | 0.8 | 0.9 |
| $CH_2=CCOO-SiCl$ with Me, Me, Me substituents | 0.6 | 0.7 |
| $CH_2=CCOO(CH_2)_3SiOOCC=CH_2$ with Me, Me, Me substituents | 1.3 | 1.4 |
| Other components | 1.8 | 1.7 |

We claim:

1. Method for purifying 3-methacryloxypropyldimethylhalosilanes comprising (I) adding (A) a Lewis acid halide to (B) an addition reaction mixture resulting from the reaction of (a) allyl methacrylate and (b) dimethylhalosilane the mixture comprising a 3-methacryloxypropyldimethylhalosilane and a 1-methyl-2-methacryloxyethyldimethylhalosilane, and (II) decomposing the 1-methyl-2-methacryloxyethyldimethylhalosilane, and (III) separating the 3-methacryloxypropyldimethylhalosilane from decomposition products of the 1-methyl-2-methacryloxyethyldimethylhalosilane by distillation.

2. A method according to claim 1, where the Lewis acid halide is selected from the group consisting of tin (IV) chloride, titanium (IV) chloride, beryllium (II) chloride, antimony (V) chloride, mercury (II) chloride, copper (II) chloride, bismuth (III) chloride, cobalt (II) chloride, calcium (II) chloride, and cadmium (II) chloride.

3. A method according to claim 1, where the Lewis acid halide is copper (II) chloride.

4. A method according to claim 1, where the Lewis acid halide is added at a concentration of 0.01 to 20 parts by weight per 100 parts by weight of the 3-methacryloxypropyldimethylhalosilane.

5. A method according to claim 1, where the Lewis acid halide is added at a concentration of 0.1 to 10 parts by weight per 100 parts by weight of the 3-methacryloxypropyldimethylhalosilane.

6. A method according to claim 1, where the decomposition of the 1-methyl-2-methacryloxyethyldimethylhalosilane is effected at a temperature within a range of 50° C. to 200° C.

7. A method according to claim 1, where the Lewis acid halide is copper (II) chloride and is added at a concentration of 0.1 to 10 parts by weight per 100 parts by weight of the 3-methacryloxypropyldimethylhalosilane, the addition reaction mixtures comprises 3-methacryloxypropyldimethylchlorosilane and 1-methyl-2-methacryloxyethyldimethylchlorosilane, and the decomposition of the 1-methyl-2-methacryloxyethyldimethylchlorosilane is effected at a temperature within a range of 50° C. to 200° C.

8. Method for purifying 3-methacryloxypropylmethyldihalosilanes comprising (I) adding (A) a Lewis acid halide to (B) an addition reaction mixture resulting from the reaction of (a) allyl methacrylate and (b) methyldihalosilane the mixture comprising a 3-methacryloxypropylmethyldihalosilane and a 1-methyl-2-methacryloxypropylmethyldihalosilane, and (II) decomposing the 1-methyl-2-methacryloxyethylmethyldihalosilane, and (III) separating the 3-methacryloxypropyldimethylhalosilane from decomposition products of the 1-methyl-2-methacryloxyethyldimethylhalosilane by distillation.

9. A method according to claim 8, where the Lewis acid halide is selected from the group consisting of tin (IV) chloride, titanium (IV) chloride, beryllium (II) chloride, antimony (V) chloride, mercury (II) chloride, copper (II) chloride, bismuth (III) chloride, cobalt (II) chloride, calcium (II) chloride, and cadmium (II) chloride.

10. A method according to claim 8, where the Lewis acid halide is copper (II) chloride.

11. A method according to claim 8, where the Lewis acid halide is added at a concentration of 0.01 to 20 parts by weight per 100 parts by weight of the 3-methacryloxypropylmethyldihalosilane.

12. A method according to claim 8, where the Lewis acid halide is added at a concentration of 0.1 to 10 parts by weight per 100 parts by weight of the 3-methacryloxypropylmethyldihalosilane.

13. A method according to claim 8, where the decomposition of the 1-methyl-2- methacryloxyethylmethyldihalosilane is effected at a temperature within a range of 50° C. to 200° C.

14. A method according to claim 8, where the Lewis acid halide is copper (II) chloride and is added at a concentration of 0.1 to 10 parts by weight per 100 parts by weight of the 3-methacryloxypropylmethyldihalosilane, the addition reaction mixtures comprises 3-methacryloxypropylmethyldichlorosilane and 1methyl-2-methacryloxyethylmethyldichlorosilane, and the decomposition of the 1-methyl-2-methacryloxyethylmethyldichlorosilane is effected at a temperature within a range of 50° C. to 200° C.

* * * * *